US006344335B1

(12) United States Patent
Tausk et al.

(10) Patent No.: US 6,344,335 B1
(45) Date of Patent: *Feb. 5, 2002

(54) LIPOSOME IMMUNOASSAY

(75) Inventors: Francisco A. Tausk, Baltimore; Howard N. Robinson, Lutherville, both of MD (US)

(73) Assignee: Leonard Bloom, Towson, MD (US); a part interest ( * ) Notice: Subject to any disclaimer, the term of this patent is extended or adjusted under 35 U.S.C. 154(b) by 0 days.

This patent is subject to a terminal disclaimer.

(21) Appl. No.: 09/280,985

(22) Filed: May 27, 1999

Related U.S. Application Data

(63) Continuation-in-part of application No. 08/951,214, filed on Sep. 19, 1997, now Pat. No. 5,919,633.

(51) Int. Cl.[7] .................... G01N 33/536; G01N 33/571
(52) U.S. Cl. ................. 435/7.1; 435/7.2; 435/7.36; 428/402.2
(58) Field of Search ............... 435/7.36, 4, 7.1, 435/7.2; 428/402.2

(56) References Cited

U.S. PATENT DOCUMENTS

| 4,483,921 A | 11/1984 | Cole |
| 4,745,074 A | 5/1988 | Schreier et al. |
| 4,978,625 A | 12/1990 | Wagner et al. |
| 5,068,198 A | 11/1991 | Gibbons et al. |
| 5,128,241 A | 7/1992 | Imai et al. |
| 5,173,406 A | * 12/1992 | Hosoda et al. ............. 435/7.72 |
| 5,221,613 A | 6/1993 | Kida et al. |
| 5,620,903 A | 4/1997 | Malick et al. |
| 5,702,913 A | * 12/1997 | Guadagno ................... 435/28 |

FOREIGN PATENT DOCUMENTS

EP    0 121 317 A1    10/1984

OTHER PUBLICATIONS

Ishmori et al., Journal of Immunological Methods, 75:351–360, 1984.*

Tomioka et al in the Journal of Immunological Methods, vol. 176 (1994) pp. 1–7.

Kelly, R., "Spirochetes and Spiral Bacteria", pp. 1093–1098 in *Clinical Diagnosis & Management by Laboratory Methods*, John Bernard Henry, M.D., ed., WB Saunders Company, Philadelphia, 1991.

* cited by examiner

*Primary Examiner*—Anthony C. Caputa
*Assistant Examiner*—Brenda G. Brumback
(74) *Attorney, Agent, or Firm*—Leonard Bloom

(57) ABSTRACT

A liposome or microsphere containing guaiac or other reagent is used in an immunoassay to detect an antigen or antibody. The guaiac or other reagent reacts with hemoglobin or other blood constituent to produce color indicating a positive result.

6 Claims, 3 Drawing Sheets

LIPOSOME IMMUNOASSAY

RELATED APPLICATIONS

This application is a continuation-in-part of our application Ser. No. 08/951,214, filed Sep. 19, 1997 and now U.S. Pat. No. 5,919,633.

FIELD OF THE INVENTION

The invention herein disclosed is directed to immunoassays involving liposomes or other microspheres.

BACKGROUND OF THE INVENTION

The basis for the invention is a modification of the Liposome Immune Lysis Assay (LILA), whose theoretical principle is the following:

1. Prior Art Method

Antibody-dependent cytotoxicity is a process mediated by immunoglobulins and a number of host proteins termed the "complement system". When antibodies recognize and bind their target, they will suffer conformational changes that activate the complement system, which will eventually result in the formation of the "membrane attack complex" on the surface of the foreign substance or cell. It is the membrane attack complex that perforates the cytoplasmic membrane and induces membrane channels that result in the lysis of the cell targeted by the antibodies. This perforation of membranes is utilized to evaluate the presence of circulating antibodies. Instead of using cells or organisms, the LILA assay uses liposomes, which are small spheres composed of lipids. These liposomes have the property of allowing a substance placed in their interior to remain hidden from the environment as long as the lipid capsule or liposome remains intact. When the capsule is destroyed or punctured, its contents are released. The prior art discloses liposomes that contain a substance which when released from the liposome will change color when contacting an appropriate substrate present in the surrounding environment. Further, liposomes may be sensitized with an antigen on their surface (i.e., cardiolipin). When the sensitized liposomes are diluted with serum of a patient with antibodies to said antigen, in this case against the syphilis antigen, i.e., cardiolipin, the antibodies recognize and attach to the surface of the sensitized liposomes, thus activating the complement present in the serum, which in turn activates the membrane attack complex. Once the complement system is activated and starts puncturing the liposome surface, the substance contained in the interior of the liposome (e.g., an enzyme that may change the color of a substrate) leaks into the surrounding solution which contains the appropriate substrate for the enzyme. The color of the substrate changes due to the enzyme acting thereon. This color change can then be measured in a spectrophotometer or a device used for reading ELISA assays. This is an ingenious assay, but it does not provide advantage over other methods such as solid phase immunoassays such as the ELISA, which are used to measure the same substance.

2. Prior Art

Tomioka et al in the Journal of Immunological Methods, Vol. 176 (1994) pages 1–7, teach immunoassay methods using liposomes using a model lipid of archaebacteria, namely, 1,2 -di(3RS,7R,11R-phytanyl)-sn-glycero-3-phosphlocholine. The advantage of this model lipid is that it could be used along with other lipids to form stable liposomes, as explained in the article.

Cole in U.S. Pat. No. 4,483,921 teaches immunoassays involving liposomes. In that assay after recognition between antigen and antibody, the liposome ruptures releasing an enzyme which is detected indicating a positive results.

Wagner et al U.S. Pat. No. 4,978,625 uses liposomes in immunoassay, however, the assay does not depend upon the rupture of the liposome.

Gibbons et al (U.S. Pat. No. 5,068,198) describes preparing liposomes to be used in immunoassays. The substance in the liposome is released, for example, by freezing and thawing, sonication or osmotic shock.

Hosoda et al (U.S. Pat. No. 5,173,406) discloses a liposome immunoassay in which complement is involved in causing the rupture of liposome. A kit for carrying out the assay is taught. Various markers used in the assay are disclosed. Hosoda et al also disclose the use of polyclonal, as well as monoclonal antibodies.

Kida et al (U.S. Pat. No. 5,221,613) disclose an immunoassay process using liposomes. The assay encapsulates an antibody in the liposome.

Malick et al (U.S. Pat. No. 5,620,903) teaches liposome assays. Water-insoluble dyes are used as the marker with water-soluble dyes added as an option.

These prior art patents show liposomes used to encompass reagents in various embodiments, however, none of the prior art reacts guaiac disposed in a liposome with blood hemoglobin.

OBJECTS OF THE INVENTION

A main object of this invention is to produce a method that will allow for the accurate and fast detection of a large number of human diseases using a very economical and simple one-step method.

A further object is to use sensitized liposomes or microspheres containing a reagent to detect a blood component.

A specific object of this invention is to use a sensitized liposome containing guaiac to react with hemoglobin in the event a specific antibody is detected.

BRIEF DESCRIPTION OF THE INVENTION

The present disclosure describes an homogeneous immunoassay designed to detect the presence of specific antibodies in whole blood. Such antibodies react with an antigen present on the surface of microcapsules such as liposomes, which enclose a reporter molecule. Subsequent to the antibody-antigen reaction, the microcapsules lyse by the action of the complement system, liberating their content which then reacts with a substance or substances present in whole blood, producing a change in color which can be visible to the naked eye.

SUMMARY OF THE INVENTION

The herein disclosed invention has a main object the rapid detection of an antigen or antibody in the blood.

Another object is to produce an immunotest which can readily detect a disease state in the body by testing blood.

The invention contemplates a test kit for immunoassay of a blood sample comprising in effective amounts:
  a) an antigen or antibody sensitized liposome containing guaiac therein,
  b) complement and
  c) hydrogen peroxide The invention also contemplates a method for detecting either an antigen or antibody in a hemoglobin-containing blood sample comprising a) providing a container containing a sensitized liposome surrounding guaiac therein, b) said container also being provided with complement and then c) adding a hemoglobin containing blood sample to be tested for a specific antigen or antibody such that if there is a reaction between the antigen or antibody on the sensitized liposome, with its specific binding partner, the liposome will rupture, releasing the guaiac to react with the hemoglobin contained in the blood to produce a blue/brown-black color indicating a positive result; and in the event there is no reaction between the specific binding partners the liposome will remain intact and the blood sample will retain its original coloration indicating a negative result. More specifically the liposome can be sensitized to syphilis.

In a broad aspect, the described invention envisions in combination, a composition to be tested comprising a blood sample and a sensitized liposome containing a reagent which will react with a blood component.

In a broad aspect, the invention involves a method for detecting either an antigen or antibody in a blood sample comprising combining said blood sample with a sensitized liposome containing a chemical agent which will react with a blood component once a specific binding partner for the sensitized liposome causes the liposome to rupture.

This invention contemplates in combination, a composition to be tested comprising a blood sample and a sensitized microsphere containing a reagent which will react with a blood component, once the microsphere is ruptured.

One aspect of this invention may be viewed as a method for detecting either an antigen or antibody in a blood sample comprising combining said blood with sensitized microspheres containing a chemical agent which will react with a blood component once a specific binding partner for the sensitized liposome causes the liposome to rupture.

Gibbons et al (U.S. Pat. No. 5,068,198) discloses materials for reversibly surrounding the reagents of this invention and are materials that are capable of temporarily confining the reagent until a reaction is effectuated and then releasing the confined reagent. Illustrative materials include lipid bilayers such as liposomes, artificial cells, vesicles, natural cell membranes such as red blood cells ghosts; gels such as gelatin and agarose; polymerized beads and the like. Applicants' invention visualizes employing these microspheres or microcapsules in their invention. Applicants also refer to U.S. Pat. No. 5,128,241 as emplifying "erythroctye ghost membrane" as an operative microcapsule to use in their invention. Note is also taken of Malick et al (U.S. Pat. No. 5,620,903) who disclose the use of silicon for forming microspheres. The disclosures of these patents are incorporated by reference into the disclosure of this application.

DETAILED DESCRIPTION OF THE INVENTION

Figure 1:
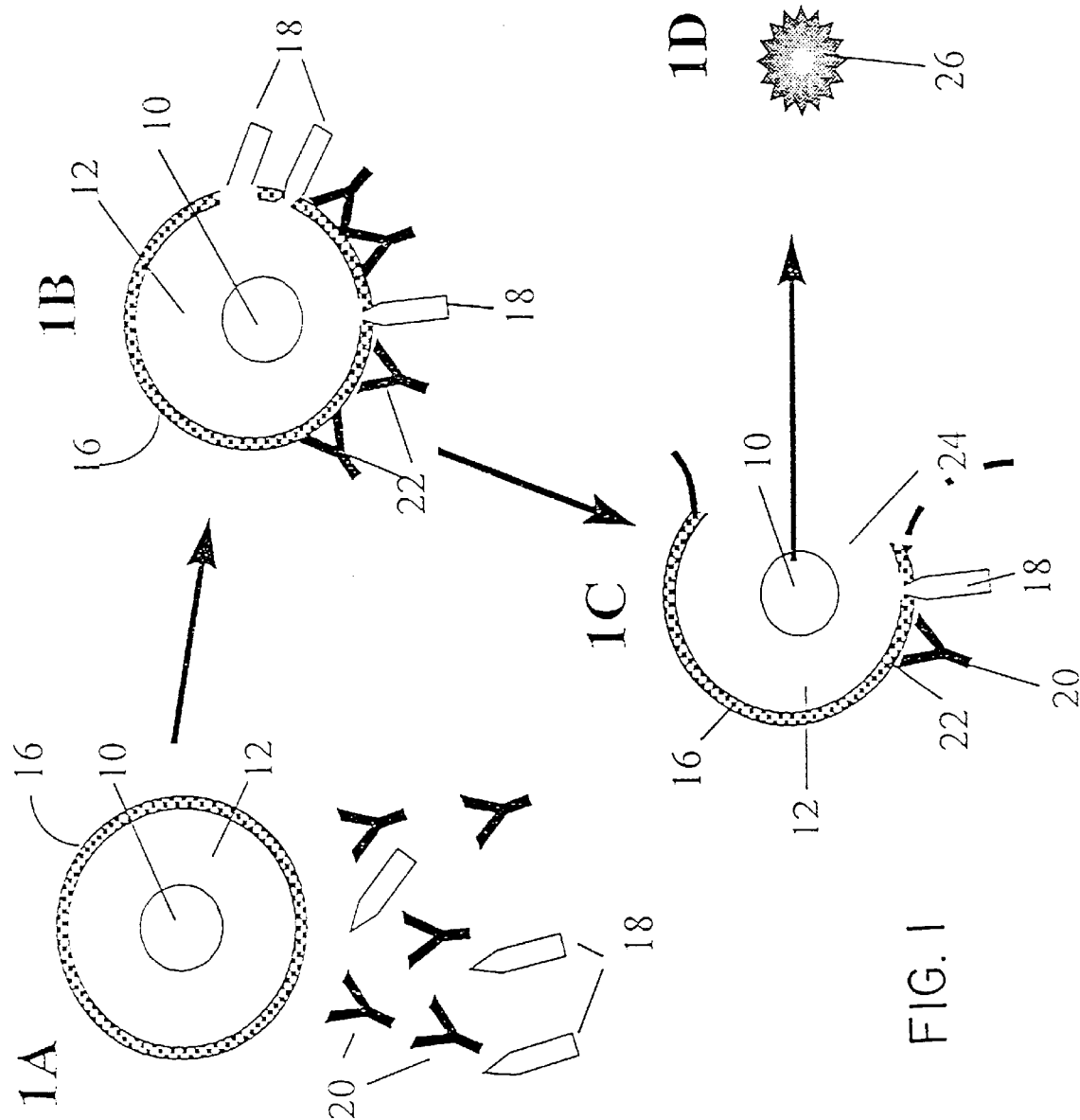
FIGS. 1A–D is a schematic representation of the reaction taking place between the liposome and blood sample to produce a color reaction.

Referring to FIGS. 1A–D, there is illustrated a schematic representation of the immunoassay of this invention which takes place in the blood. The immunoassay involves the release of guiaiac 10 from a sensitized liposome 12. In FIG. 1A guaiac 10 is disposed in a sensitized liposome 12 which is sensitized with an antigen 16 (for example, syphilis antigen, etc.). The antigen sensitized liposome 12 is disposed with blood which is the media with which the immunoassay takes place. In the blood along with the antigen and sensitized liposome 12 are complement 18 and antibodies 20. The antibody 20 recognizes its specific binding partner, namely, the antigen 16, on the liposome 12 and binds to the antigen 22 (FIG. 1B). Once there is binding between the antigen and antibody 22 on the liposome 12 in the presence of complement 18, the liposome 12 ruptures as at 24 releasing guaiac 10 (FIG. 1C) which, in turn, is oxidized by hemoglobin in blood in the presence of peroxide causing the guaiac to turn blue 26 (FIG. 1D).

Figure 2:
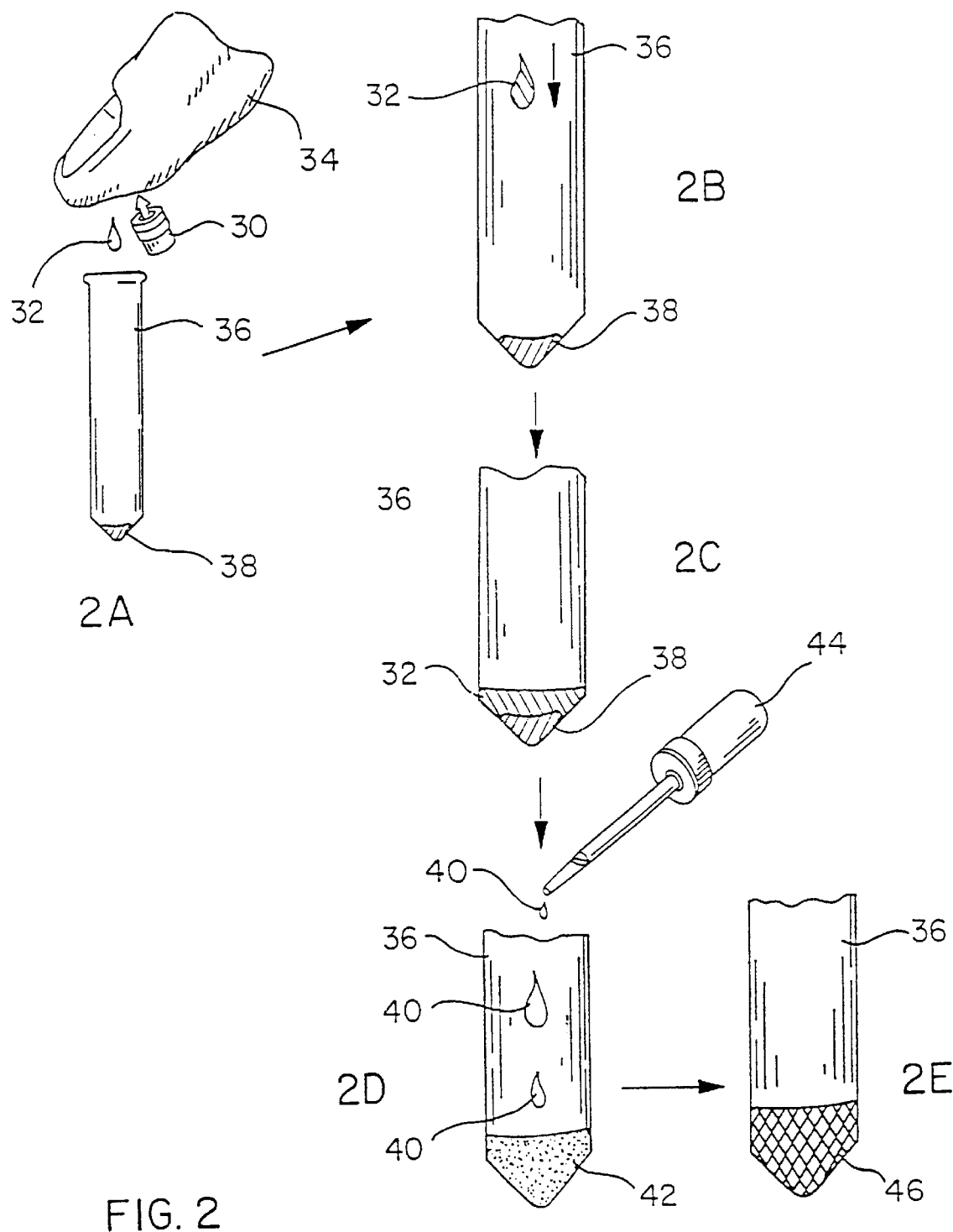
FIGS. 2A–E is a schematic representation of the steps required to carry out the test.

With reference to FIG. 2 A–E a lance 30 is used to obtain blood 32 from the finger 34 of a patient to be tested (FIG. 2A). The blood 32 drops into a test-tube 36 which has sensitized guaiac-containing liposomes 38 at the bottom of the test-tube 36 (FIG. 2B). The blood 32 is mixed with guaiac-containing liposomes 38 (FIGS. 2 C–D). Referring to FIG. 2D, hydrogen peroxide 40 is added to the mixture of liposomes and blood 42 with dropper 44. If the test is positive, a blue color 46 will form in the bottom of the test-tube 36.

The method of this invention uses the same principle as the liposome/immunoassay of the prior art detailed above; however, the method of this invention will embody test tubes containing the liposomes that bear on their surfaces the antigen of interest. These liposomes contain in their interior guaiac or a derivative of guaiac which changes color from transparent or light blue to dark blue when coming in contact with hemoglobin and peroxide. The liposomes may be in a suspension containing ammonium chloride or hypotonic saline or alternatively, normal saline (used to lyse the red cells and expose the hemoglobin) in a vacuum tube. The patient's blood will be drawn into such a tube. Without any further manipulation, the tube is allowed to stand at room temperature for 5–20 minutes (or alternatively at 37° C., to accelerate the reaction). During this period of time the reaction takes place. If the patient has the disease (that is, he carries antibodies against the specific antigen sensitized to the antigen) the color of the liquid in the tube containing the patient's blood will change from red to dark blue/brown-black. The mechanism of action is that if the patient has antibodies to the specific antigen which sensitized the liposomes, the antibodies will bind to the surface of the liposomes and induce their complement mediated lysis, releasing the guaiac reagent. When the guaiac leaks from the liposomes, and reacts with the hemoglobin, a blue color is produced in the presence of peroxide, indicating that the test was positive. We envision the possibility of adding to the test tube exogenous complement (such as guinea-pig serum) if the reaction requires additional complement source.

In one aspect, this invention involves peroxide and a liposome containing guaiac therein. This could be a commercial product sold to suppliers for use in laboratories and doctors' offices. The liposome containing gulaiac could be sensitized with a specific antigen or antibody. The amount of guaiac in the liposome is not critical, but there should be an amount adequate to show a color reaction with hemoglobin. The specific antigen or antigen may be syphilis. The invention embraces a test kit for immunoassay of a blood sample comprising:

a) an antigen or antibody sensitized liposome containing guaiac therein, and b) complement The invention envisions a method for detecting either an antigen or antibody in a hemoglobin-containing blood sample comprising a) providing a container containing a sensitized liposome surrounding guaiac therein, b) said container also being provided with complement and peroxide and then c) adding a hemoglobin containing blood sample to be tested for a specific antigen or antibody such that if there is a reaction between the antigen or antibody on the sensitized liposome with its specific binding partner, the liposome will rupture, releasing the guaiac to react with the hemoglobin contained in the blood thus producing a blue color indicating a positive test; and in the event there is no reaction between the specific binding partners, the liposome will remain intact and the blood sample will retain its original coloration indicating a negative result.

Liposomes are small phospholipid bilayer vesicles that are capable of carrying lipophilic or hydrophilic molecules in their interior. As long as the vesicle is intact, its content is not in contact with the exterior milieu. If, however, the liposome's surface is perturbed, the internal molecules are released and exposed to the external milieu and react therewith to produce the assay result. The production of stable liposomes is well known to the art (see above mentioned references as well as Schreier et al, U.S. Pat. No. 4,745,074.)

When attempting to detect the presence of a circulating antibody, the liposomes will bear on their surface the antigenic structures that are recognized by such antibody. These antigens can either be incorporated with the liposome during their production (for example, by including cardiolipin in the liposome composition for the detection of syphilis antibodies), or alternatively, they may be cross-linked to the surface of the liposomes as taught by Imai et al (U.S. Pat. No. 5,128,241); see also Schreier et al (vide supra).

The lytic component of the blood will be mediated by the proteins of the complement system. When the antibodies present in the blood attach to the antigen on the liposome surface, the complement system becomes activated, resulting in the lysis of the liposomes, releasing the marker substance to the exterior. A proportion of the liposomes may lack the inclusion of the marker in their interior, so as to reduce the non-specific lysis of the marker-containing liposomes.

The marker molecule which will be present in the interior of the liposomes will be such that it can react with a substance present in the whole unfractionated blood, and with or without the addition of any further developer, will change the color of the whole reaction mixture in such a manner that it will be clearly visible to the naked eye without the need of special instrumentation or any further manipulation.

All required reagents are available commercially. The manufacture of liposomes of predetermined specifications, with or without the presence of internal markers and ligation of surface antigens, can be ordered from companies which provide these services. The antigens to be used can be purchased commercially or manufactured following prior art.

EXAMPLE

Blood from a patient infected with syphilis will be obtained by the puncture of the fingertip utilizing a commercially available lancet. A drop (20 microliters) of said blood will be deposited in a small vial. Three drops of distilled water (which may be optional) will be added to the vial in order to lyse the red cells, and subsequently 3 drops of a liposome mixture will be applied the liposomes in a concentration of 0.1 micromoles of lipid per 100 microliters of reaction volume will be small unilamellar vesicles including cardiolipin (syphilis antigen) as a constituent, containing a saturated aqueous solution of guaiac gum (purchased form Sigma, St. Louis, Mo.) in their interior. Such liposomes will be suspended in an isotonic solution of phosphate buffered saline containing thimerosal as preservative. The reaction mixture will be incubated for a period between 5 and 20 minutes at temperatures that may range between 22 and 37 degrees centigrade. At that point, a drop of 3% concentration of hydrogen peroxide in saline will be added, and in approximately 30 seconds the whole mixture will be examined to note any change in color from red (negative reaction) to dark brown/black (positive reaction, indicating that anti-cardiolipin antibodies were present in the blood).

An assay such as the above described will be available in the form of a kit, so that 3 wells will be available for deposition of a drop of test blood. Well #1 will receive the reagents described above. Well #2 will be the negative control, in which the liposomes will lack cardiolipin in their structure, and a positive control in well #3, which will be identical to #1, with the addition of one drop of a solution of commercially available goat anti-cardiolipin immunoglobulin at a concentration of 1 milligram per milliliter. These positive and negative controls will allow the appropriate evaluation of the tested blood. Well #2 should remain red colored, and well #3 should turn dark brown/black.

This kit will have the following reagents:

1) Blood lancet.
2) A small tray with 3 wells with a total capacity of approximately 250 microliters each.
3) A dropper bottle containing cardiolipin labeled liposomes with guaiac solution in their interior mixed with an excess of empty unlabeled liposomes.
4) A dropper bottle with distilled water.
5) A dropper bottle with a mixture of unlabeled liposomes containing and lacking guaiac in their interior.
6) A dropper bottle with 3% hydrogen peroxide.
7) A dropper bottle with anti-cardiolipin immunoglobulins.
8) A small incubator that maintains the temperature of the reaction mixture at 37° C.

The principle of the assay is based on the use of lipid microspheres that will be sensitive to attack by complement proteins assembled on their surface. It requires the use of very stable material, so that it does not leak out its contents spontaneously or leak as a result of storage aging. Although the technology of liposomes is relatively old, there are many products that have patents based on their improvement in performance. For example, U.S. Pat. No. 5,620,903 to Malik et al teaches the production of stabilized microspheres. There are many different ways to make liposomes or microspheres known in the art.

There are substances besides guaiac which will react with hemoglobin. Examples of these are chromogens that change color in the presence of the peroxidative activity of hemoglobin. These are Ortho tolidine, benzidine, Ortho dianisidine, diaminobenzidine, phenylenediamine and tetramethylbenzidine. All these methods require the presence of an oxygen donor in the form of hydrogen peroxide or hydroperoxide as described in Pugia (U.S. Pat. No. 5,362,633) and a ferric ion. Other indicator dyes such as phenothiazine, phenolphtalein and thiazolinone hydrazone among others will be operative.

The numerous kits for the detection of blood cells in urine utilize mostly benzidine derivatives. All the reagents are attached to the "dip-strip" which when dipped into the urine changes color in the presence of red cells. The tests for occult blood in stool use either benzidine derivatives, or guaiac. The latter is chosen because it has lower sensitivity and thus gives less false positives (in our case, even a minor leakage of reagents from the liposomes should not induce a change in color). As an indication of the sensitivity of guaiac to hemoglobin, there is a patent that teaches a VASELINE™ (Solid petrolatum) based ointment containing guaiac and peroxides, so that when performing a rectal exam, the exploring finger glove will change color if occult blood is present in the rectum. The prior art teaches the production of kits to detect red blood cells (occult blood) in body fluids.

Blood constituents other than hemoglobin are envisioned as being able to react with reactants contained in the liposome or microspheres. For example, the invention envisions a chromogen in the liposome that reacts with protein. The liposomes could contain an appropriate solution Coomassie blue, and if the blood to be tested has antibodies that induce complement to perforate the liposomes and release the Coomassie blue, this light orange-red substance would come in contact with the large amount of proteins in the blood and change color to become dark blue/green, thus changing the color of the blood sample to blue/black. This would be a very simple assay, as there are large amounts of proteins in the blood.

There are other substances in the blood which could potentially react to some indicator in the liposomes. One could test for the activity of various blood enzymes, for the presence of minerals and metals such as iron, and the list is very long. One could insert a colorant for iron in the liposomes, and develop the reaction by the color produced by contact with iron upon rupture of the liposomes/micro spheres.

The invention herein disclosed covers the detection of many diseases. Basically any infectious disease or autoimmune disease in which the subject develops antibodies to a known blood antigen. For example, all infectious diseases that are currently detected with the use of immunoassays such as ELISA or other such tests. These include: AIDS, Brucellosis, Tularemia, Plague, Glanders, Melioidosis, Anthrax, Typhoid fever, Tetanus, leptospirosis, syphilis, Rocky mountain spotted fever, pneumococccal pneumonia, menningococcemia (viral and bacterial), mycoplasma pneumonia, psittacosis, Coxsackievirus, echovirus, Parvovirus, Cytomegalovirus, measles, rubella, varicella, cat-scratch disease, Lyme disease, ehrlichiosis, hepatis B, hepatitis C, Hepatitis D, cryptococcosis, coccidioidomycosis, histoplasmosi, actinomycosis, nocardiosis, sleeping sickness, Chagas' disease, Leishmaniasis, Toxoplasmosis, Amebiasis and others.

Autoimmune diseases that could be diagnosed through this method include: Systemic Lupus Erythematosus, Rheumatoid Arthritis, Sjogren's Syndrome, Pemphigus, Bullous pemphigoid, and any other disease presenting circulating autoantiboidies.

Any other disease in which a circulating substance can be detected utilizing specific antibodies. For example, detection of circulating cancer antigens by attaching specific antibodies to the surface of the liposomes. Or similarly, detection of viral particles (as in HIV) in blood. Moreover, this method may be utilized in the detection of chemical agents, as well as pharmaceutical or illegal drugs in the circulation.

The invention herein disclosed envisions the guaiac contained by the liposomes, and the hydroperoxide sitting by itself free in the test tube, or have the peroxide in the liposomes, and the guaiac free in the tube, or a mixture of some liposomes with guaiac and others with peroxide, or both in the same liposomes, or lastly, one of the ingredients could be added from a dropper to the tube after the blood extraction, however, this would add another step albeit a simple one.

One of the main ideas of this invention is to avoid using equipment that reads optical densities or wave lengths, and develop a test that is revealed clearly to the unaided eye. Yet there are ways to facilitate the test. For example: one could have a small vial into which a drop of blood obtained from a finger-stick is deposited as described in the example. The drop of blood would change color as the reaction proceeds. The advantage of this would be that only one drop of blood needs to be obtained, thus avoiding the phlebotomy. This method is extensively used in kits for home blood glucose measurements (actually now also used for home AIDS test). Another advantage is that since there is no tube to open, it is easy to add a drop of a reagent to a blood drop in a vial. In the event that one prefers a test in which a reagent or reagents are added exogenously, this would probably allow for better control of the amounts of reagents to be utilized. A negative and positive control test vial will be included with the kit, to guarantee the lack of false positive or negative reactions.

Another instrument that would be of interest would be to have a warming block at 37 degrees to facilitate and accelerate the reaction. This should not be very complicated or expensive, and could be provided with the kit.

There are many advantages to this invention:

The test is an all or nothing response and is very easy to perform in a single step.

It is self contained, requires no training or special equipment to interpret results.

The test can be sold as a self standing kit, and would be particularly useful in settings that don't have highly specialized medical care facilities. For some applications such as in AIDS, Syphilis, Lupus Erythematosus, Rheumatoid Arthritis, Hepatitis, Lyme's disease, Rocky Mountain Spotted Fever, as well as drug monitoring, this test could become of routine use in laboratories and in physicians' offices.

The test is very rapid to perform. All that is necessary is to draw blood into a stored tube containing sensitized liposomes, complement, etc. and wait 5–20 minutes for test results.

The test is easy to read because there is a change of the color of the blood to blue/black positive (+), or the color does not change at all indicating negative (–).

The test does not require trained personnel. The nurse or technician that draws the blood is able to read the color change.

The test may be used for detecting numerous diseases: For example, infectious diseases of a known organism (AIDS, syphilis, hepatitis, etc.); autoimmune diseases with circulating antibodies (Lupus, Rheumatoid Arthritis, etc.)

The test does not require sending a blood sample to a central laboratory for analysis. So that not only is the test rapid, it is relatively inexpensive and effects substantial cost savings in the health care industry.

This invention allows for the first time a change of the color in whole blood in an immunoassay; while all elements of blood are present, and not having to separate the components or manipulate or treat the blood sample prior to conducting the test.

The inventors have continued to make improvements to their invention.

Figure 3:
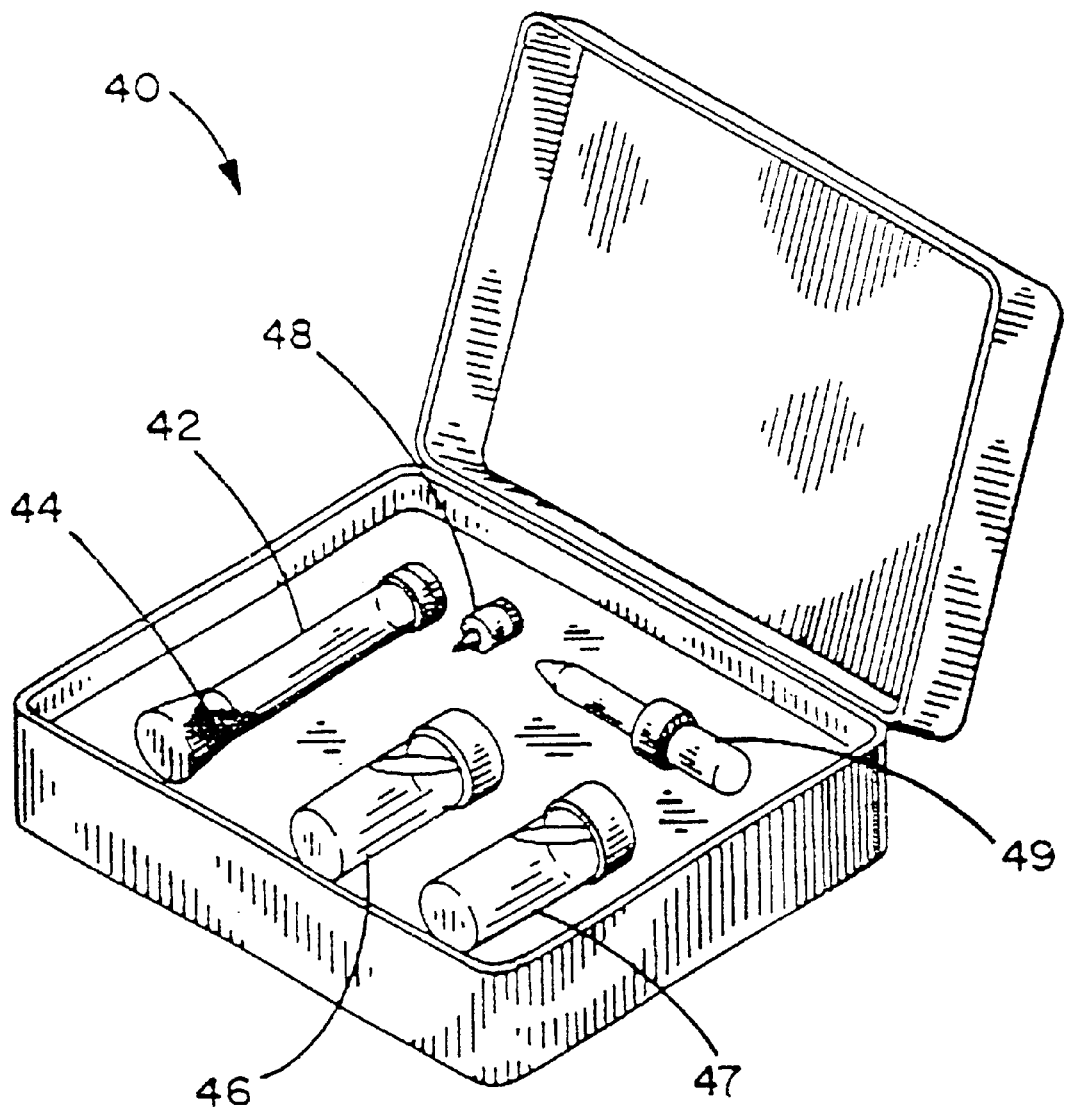
FIG. 3 is a view illustrating a kit containing components necessary to carry out the immunoassays of this invention.

Shown in FIG. 3 is an alternative kit 40 of components for carrying out the immunoassay of this invention. The components are a test-tube 42 containing therein sensitized liposomes 44. The sensitized liposomes can contain therein guaiac, a selected dye to react with a blood component or a peroxide such as hydrogen peroxide. The peroxide contained in the sensitized liposome is to be used in a special manner described herein. The kit will contain peroxide solution 46 when the sensitized liposome contains guaiac; or contain guaiac when the liposome contains peroxide therein. For special circumstances where the blood sample may not contain adequate complement a container of complement in solution 47 is provided. In addition, the kit contains a lancet 48 for obtaining the blood sample from the patient and a dropper 49 for use for applying reagents to test-tube 42.

A further example of a kit is to be:

A Vacutainer™ (trademark of Becton-Dickinson) Tube containing
1) sensitized liposomes or liposomes containing the appropriate antigen on their surface with a chromogen (e.g. Guaiac) in the interior of the liposome and
2) Hydroperoxide (i.e. hydrogen peroxide)

The kit will be used in the following manner:

A blood sample is obtained by venipuncture into a Vacutainer™ tube. After lightly shaking, the tube will be maintained at 37 degrees centigrade or alternatively at room temperature. The antibodies bound to the liposome surface will recognize its antigen and will mediate the activation of complement and the subsequent lysis of the liposomes releasing the chromogen to react with the hemoglobin in the presence of Hydroperoxide (hydrogen peroxide). Changing of the color of the chromogen indicates a positive test result.

In an embodiment of this invention, the blood sample to be used in the test is obtained from a drop of blood obtained from a finger-stick, i.e., venipuncture into a Vacutainer™ tube. Enclosing all of the reactants in the tube as an "all in one" will allow the assay to be performed in an enclosed tube with no need to manipulate the sample or add reagent since all reagents will be enclosed in the single tube.

In a further alternative embodiment, there will also be a reagent in the tube which will mediate the lysis of the red cells (i.e., ammonium chloride, water hypotonic buffers, etc.).

As an additive to the tube, there may be included an agent that will prevent the coagulation of the blood sample (i.e., citrate, heparin, etc.). It is to be understood that the anticoagulant component should not interfere with any activation component such as complement, etc.

In an elegant embodiment of this intension, the Hydroperoxide (i.e., hydrogen peroxide) is contained within the liposomes, and the chromogen (i.e., guaiac) is present freely in the mixture in the tube, that is exterior to the liposome. In other words, the reagent which gets liberated is the peroxide which facilitates the reaction between the chromogen and the hemoglobin.

The inventors envision encapsulating specific enzymes into the liposome. The enzymes in turn will react with a blood protein and be a component in bringing about the reaction.

In an elegant embodiment of this invention, the chromogen is adhered to the glass wall of the tube in the form of a plus sign (for example), and the change in color of such area or sign may be visualized from the exterior of the glass tube once a positive reaction has taken place.

Other chromogens: Many substances can be incorporated in the liposomes so that upon their lysis, the released substance changes color due to their recation with components of the blood. For example, Coomassie Blue could be encapsulated, and upon release, will change to dark blue when in contact with blood proteins. One skilled in the art could cite many other substrates that could be acted upon by enzymes in the blood, or other chromogens that will change color when in contact with blood substrates and blood elements.

An embodiment of this invention visualizes a variation of the test in which the liposome is not sensitized. In this embodiment, the inventors utilize liposomes that contain the chromogen. However, the liposomes have not been sensitized and do not contain an antigen on the liposome surface. The antigen will be free in the tube. The activation of complement in the mixture will be sufficient to induce the lysis of the liposomes, without necessitating their sensitization. This is based on the principle of passive lysis, or bystander lysis, and is due to the lack of regulatory (control) proteins on the surface of the liposomes (contrary to what occurs on normal human cells).

Same as above but including substances that will prevent the complement inhibition by inactivating control proteins of the serum (such as anti-Factor I Fab '2).

Detection of circulating antigens (i.e., HIV, Hepatitis Virus, etc.) The liposomes would not be sensitized. The Vacutainer™ tube will contain a mixture that will include the presence of purified sheep or rabbit antibodies in the form of IgG or IgM against the antigen of interest (such as anti-HIV). The antigen will be recognized by the antibodies, and the formation of immune-complexes will activate the complement system, resulting in bystander lysis of liposomes containing chromogen or hydrogen peroxide (depending on the method of detection utilized).

Obviously, many modifications may be made without departing from the basic spirit of the present invention. Accordingly, it will be appreciated by those skilled in the art that within the scope of the appended claims, the invention may be practiced other than has been specifically described herein.

We claim:

1. A liposome containing guaiac therein.

2. The liposome of claim 1 sensitized to cardiolipin.

3. A method of detecting either an antigen or antibody in a hemoglobin-containing blood sample comprising
   a) providing a container comprising an antigen or antibody-sensitized liposome surrounding guaiac therein, said container further comprising complement, and
   b) adding a blood sample which contains hemoglobin and which is to be tested for a specific antigen or antibody to said container, such that if the antigen or antibody on the sensitized liposome contacts its specific antibody or antigen binding partner in the blood sample, the liposome ruptures, releasing the guaiac therein to react with the hemoglobin contained in the blood sample producing a blue/brown-black color as an indication of a positive test result and if the antigen or antibody on the sensitized liposome does not contact its specific antibody or antigen binding partner in the blood sample, the liposome remains intact and the blood sample retains its original color as an indication of a negative test result.

4. The method of claim 3 wherein the liposome is sensitized to cardiolipin.

5. In a method for detecting either an antigen or antibody in a hemoglobin-containing blood sample, the improvement comprising combining said hemoglobin-containing blood sample with a liposome sensitized by an antigen or antibody, said liposome containing a combination of guaiac and hydroperoxide which will react with hemoglobin once a specific binding partner for the sensitized liposome in said blood sample causes the liposome to rupture allowing the combination of guaiac and hydroperoxide to react with the hemoglobin thus indicating a positive test reaction.

6. A method for detecting either an antigen or antibody in a hemoglobin containing blood sample, said method comprising adding to an antigen or antibody sensitized liposome containing peroxide therein, guaiac and a hemoglobin containing blood sample such that, if the antigen or antibody sensitized liposome containing peroxide therein contacts its binding partner in the blood sample, the liposome will rupture releasing the peroxide to cause the guaiac to react with hemoglobin and change color thus indicating a positive test reaction.

* * * * *